United States Patent [19]

Jang et al.

[11] Patent Number: 5,117,831
[45] Date of Patent: Jun. 2, 1992

[54] VASCULAR CATHETER HAVING TANDEM IMAGING AND DILATATION COMPONENTS

[75] Inventors: Yue-Teh Jang, Fremont; Eugene E. Jennings, Palo Alto, both of Calif.

[73] Assignee: Cardiovascular Imaging Systems, Inc., Sunnyvale, Calif.

[21] Appl. No.: 500,641

[22] Filed: Mar. 28, 1990

[51] Int. Cl.⁵ .................................................. A61B 8/12
[52] U.S. Cl. ........................... 128/662.06; 128/660.03; 604/96
[58] Field of Search .............. 128/660.03, 662.06; 73/623; 604/96-103; 606/191-192

[56] References Cited

U.S. PATENT DOCUMENTS

| | | | |
|---|---|---|---|
| 3,938,502 | 2/1976 | Bom | 128/662.06 |
| 4,494,549 | 1/1985 | Namba et al. | 128/662.06 |
| 4,576,177 | 3/1986 | Webster, Jr. | 128/662.06 |
| 4,794,931 | 1/1989 | Yock | 128/662.06 |
| 4,841,977 | 6/1989 | Griffith | 128/662.06 |
| 4,911,170 | 3/1990 | Thomas, III et al. | 128/662.06 |
| 4,947,852 | 8/1990 | Nassi et al. | 128/662.06 |
| 5,000,185 | 3/1991 | Yoch | 128/662.06 |
| 5,046,503 | 9/1991 | Schneiderman | 128/662.06 X |
| 5,049,130 | 9/1991 | Powell | 128/662.06 X |

*Primary Examiner*—Francis Jaworski
*Attorney, Agent, or Firm*—Townsend and Townsend

[57] ABSTRACT

A combined ultrasonic imaging and dilatation catheter includes an inflatable dilatation balloon located at the distal end of a flexible catheter body. An ultrasonic imaging system including a fixed ultrasonic transducer and a rotatable reflective surface capable of deflecting an ultrasonic signal from the transducer is located adjacent to, but axially spaced-apart from the dilatation balloon. The dilatation balloon in the interior of the imaging housing are isolated, and separate lumens are provided for inflating the balloon and flushing the imaging housing. In this way, the balloon may be inflated with a contrast medium suitable for fluoroscopic imaging, while the imaging housing may be filled with a different medium suitable for ultrasonic imaging.

20 Claims, 2 Drawing Sheets

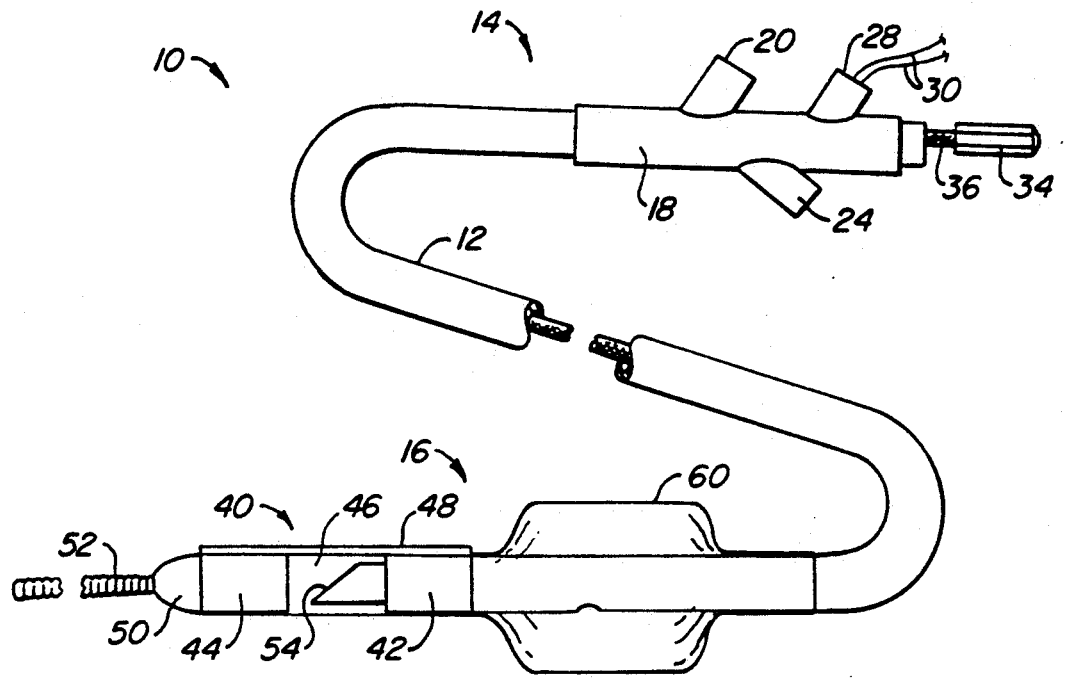
FIG._1.
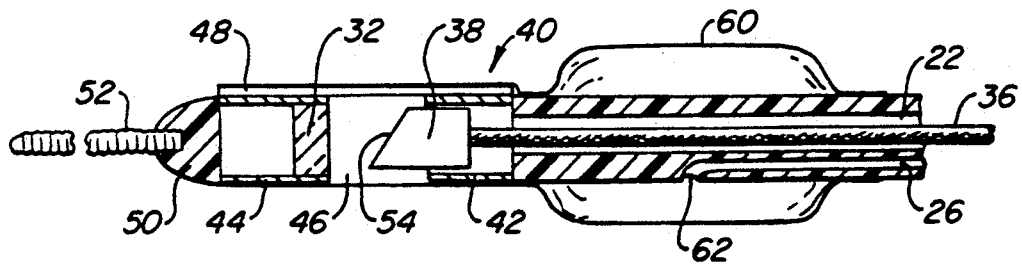
FIG._2.
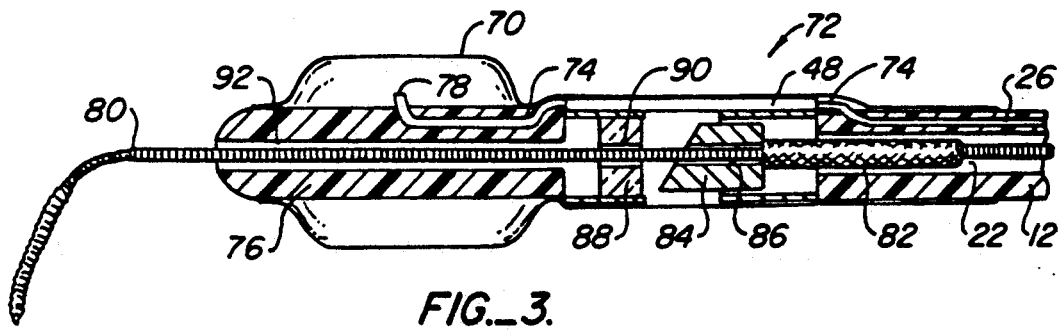
FIG._3.

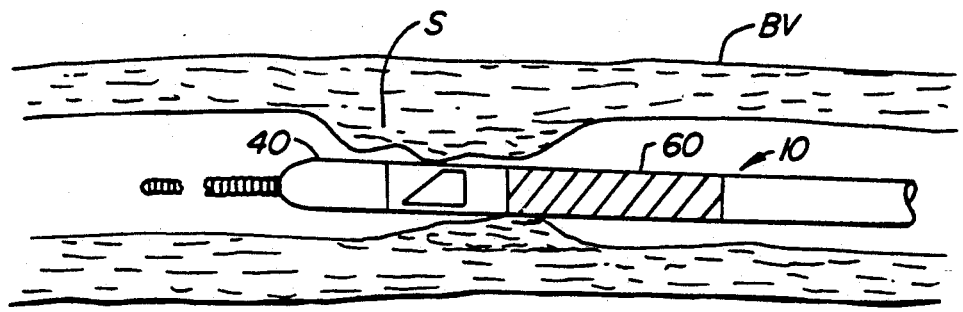
FIG._4.
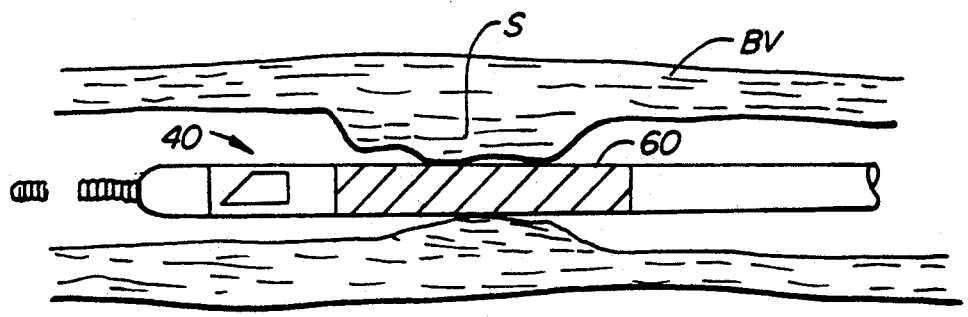
FIG._5.
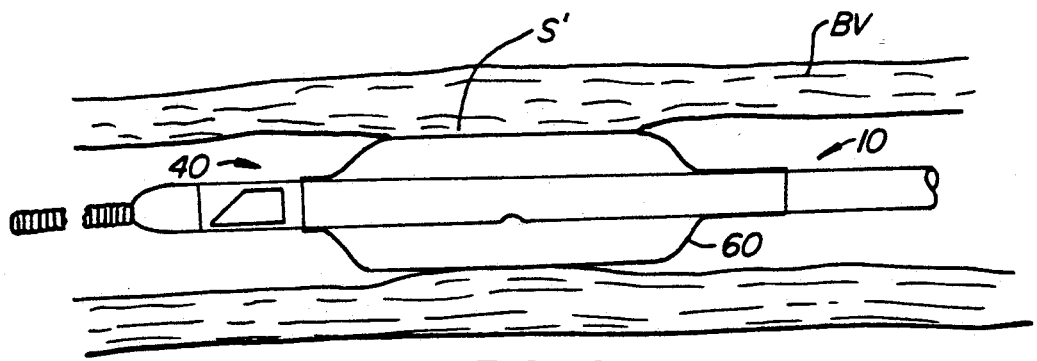
FIG._6.
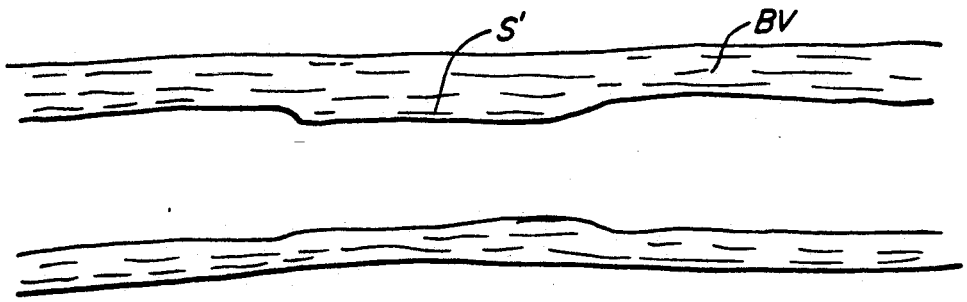
FIG._7.

VASCULAR CATHETER HAVING TANDEM IMAGING AND DILATATION COMPONENTS

BACKGROUND OF THE INVENTION

1. Field of the Invention

The present invention relates generally to the construction and use of vascular catheters, and more particularly to a vascular catheter which combines ultrasonic imaging and balloon dilatation capabilities.

Percutaneous transluminal angioplasty (PCTA), commonly referred to as balloon angioplasty, was first used successfully by Andreas Gruntzig about ten years ago and has enjoyed widespread use and success since that time. Despite its success, there are patient risks involved with balloon angioplasty. In particular, expansion within the blood vessel caused by inflation of the dilatation balloon can cause damage to the blood vessel wall and, after the procedure is complete, loose material which results from tearing of the plaque or atheroma can move into the blood vessel lumen, causing abrupt reclosure. Either event can require immediate surgical intervention. Even in angioplasty procedures which are free from adverse events, a restenosis rate of approximately 30% within six months has been observed.

It is believed that some or all of these problems may be avoided by intraluminal imaging of the treated blood vessel before, during, and after the angioplasty procedure takes place. In particular, ultrasonic imaging allows the determination of the nature of the stenotic material (e.g., the extent of calcification) as well as providing a two-dimensional profile of the stenosed region which can reveal the boundary between the stenotic material and the blood vessel. With such information, the extent of dilatation required can be more accurately forecast, lessening the chance of injury to the blood vessel. Moreover, after treatment, it is possible to examine the blood vessel wall to determine if loose stenotic material is likely to become dislodged and result in abrupt closure of the blood vessel. If such a situation exists, additional treatment can be provided and/or the patient may be observed more closely.

At least in part to provide such advantages, ultrasonic imaging catheters have been developed. See, e.g., U.S. Pat. Nos. 4,794,931; 4,576,177; and 3,938,502, the disclosures of which are described hereinbelow and are incorporated herein by reference. By using such imaging catheters together with separate angioplasty catheters, it is possible to image before and after the angioplasty procedure takes place. The use of separate imaging and angioplasty catheters, however, is problematic since it requires catheter exchange procedures which are both costly and time consuming. Additionally, the repeated insertion and removal of the catheters may exacerbate the injury to the blood vessel and may actually dislodge compressed stenotic material, resulting in reclosure of the blood vessel.

Thus, it would be desirable to combine both ultrasonic imaging and balloon dilatation capabilities on a single catheter which would allow both imaging and dilatation to be accomplished without need to exchange catheters.

U.S. Pat. No. 4,841,977, discussed hereinbelow, discloses such a catheter which combines balloon dilatation and ultrasonic imaging capabilities. A phased-array ultrasonic transducer is located within a dilatation balloon, and the patent describes that imaging may be accomplished using the ultrasonic transducer even while the balloon dilatation takes place. While that may be case, the device described in the '977 patent suffers from a particular problem.

As the ultrasonic transducer is located within the dilatation balloon, the environment surrounding the transducer will be determined by the inflation medium which is utilized. The patent suggests that either saline (which is a good ultrasonic imaging medium) or contrast medium (which is a good fluoroscopic imaging medium) may be used. It is possible, however, to use only one medium at a time and a choice must be made between having an adequate ultrasonic medium and a medium which allows the balloon to be observed by fluoroscopy during the dilatation procedure. The need to make such a choice is an unfortunate compromise in the design of the combined imaging and dilatation catheter of the '977 patent. An additional drawback to the design described in the '977 patent is the increased device diameter which results from the presence of the uninflated balloon over the distal imaging housing. Such increased diameter limits the ability of the catheter to cross particularly tight lesions which may be present in the blood vessel being treated.

For these reasons, it would be desirable to provide combined ultrasonic imaging and dilatation catheters which can use a suitable contrast medium for balloon inflation while maintaining the ultrasonic transducer in an environment optimized for imaging. It would be particularly desirable to provide vascular catheters having reduced diameters where the balloon and ultrasonic transducer are axially spaced-apart and where different media may be introduced to the region surrounding each of the balloon and the ultrasonic transducer.

2. Description of the Background Art

U.S. Pat. No. 4,794,931, describes a combined atherectomy-ultrasonic imaging catheter where a cross-sectional vascular image is obtained substantially at the location where a stenosed region is severed by a rotating blade. Although a balloon is located next to the blade and the imaging transducer, that balloon is intended for positioning of the blade and not for dilatation. U.S. Pat. No. 4,841,977, describes an angioplasty catheter having a phased-array ultrasonic imaging transducer located within a dilatation balloon. U.S. Pat. No. 4,494,549, describes an endoscope having an ultrasonic imaging transducer located within a balloon at its distal end. The ultrasonic signal from the transducer is reflected outwardly by a rotating inclined surface. Other ultrasonic imaging catheters are described in U.S. Pat. Nos. 3,938,502, and 4,576,177.

SUMMARY OF THE INVENTION

A catheter and method for ultrasonic imaging and dilatation of stenosed regions in a patient's vascular system are provided. The catheter comprises a flexible catheter body having proximal and distal ends and, usually, at least two lumens extending therebetween. A dilatation balloon is located at a first axial position generally at the distal end of the catheter body. An ultrasonic scanning unit is also located generally at the distal end of the catheter body, but is spaced axially apart from the dilatation balloon. The balloon and the region surrounding the ultrasonic scanning unit are isolated, and separate means are provided for introducing fluid into each, usually employing the separate lumens in the catheter body. In this way, contrast medium can be introduced to the dilatation balloon to enhance fluoroscopic imaging while a medium suitable for use in ultrasonic imaging, such as saline or water, can be introduced to the region surrounding the ultrasonic scanning unit.

Using such a catheter, a stenosed region in a blood vessel can be treated as follows. The catheter is positioned within the patient's vascular system so that the ultrasonic scanning unit lies within the region of stenosis. An image of the stenosed region is then obtained, revealing information which is useful in planning the dilatation procedure which follows. The catheter is next repositioned so that the dilatation balloon lies within a stenosed region, and the balloon is inflated with a suitable fluorescent contrast medium. In this way, the degree of balloon inflation and its effect on the surrounding stenotic material can be monitored by conventional fluoroscopy during the angioplasty procedure. After the procedure is complete, the catheter can again be repositioned so that the ultrasonic scanning unit is returned to the now expanded stenosed region. The region can be examined for evidence of damage to the vessel wall as well as to determine the likelihood that abrupt reclosure may occur.

BRIEF DESCRIPTION OF THE DRAWINGS

FIG. 1 illustrates a combination of dilatation and imaging catheter constructed in accordance with the principles of the present invention.

FIG. 2 is a detail view of the distal end of the catheter of FIG. 1, shown in sectional elevation.

FIG. 3 illustrates an alternative configuration for the distal end of the catheter of FIG. 1, shown in cross-sectional elevation.

FIGS. 4–7 illustrate the method of the present invention for treating stenosed regions within a blood vessel using the catheter of FIG. 1.

DESCRIPTION OF THE SPECIFIC EMBODIMENTS

Catheters constructed in accordance with the principles of the present invention will comprise an elongate flexible catheter body having a proximal end and a distal end, and an imaging housing and dilatation balloon located at the distal end of the catheter body. The catheter body will comprise a highly flexible structure capable of insertion into and manipulation within a patient's vascular system. The dimensions of the catheter will depend on use, with length varying widely, typically being between about 40 cm and 150 cm, usually being between about 90 cm and 140 cm. The catheter tube diameter may also vary widely, typically being between about 2 F (French) and about 12 F, usually being between about 5 F and 9 F, and more usually varying from about 6 F to 8 F (1 French=0.013 inches), with catheters for peripheral arteries generally being larger. The flexible catheter tube may be composed of a wide variety of biologically compatible materials, particularly being made from polymers such as silicone rubber, natural rubber, polyvinyl chloride, polyethylene, polyurethanes, polyesters, polytetrafluoroethylene, and the like. Frequently, the catheter tube may be a composite material having a reinforcement material incorporated therein in order to achieve the desired strength, flexibility, and toughness. Suitable catheter tubes will normally be formed by extrusion, with one or more integral lumens being provided. The catheter diameter can then be modified by heat expansion and shrinkage using conventional techniques. The construction of suitable vascular catheters is well described in the patent and medical literature. The catheter tube is joined to a generally rigid housing at its distal end. The housing may be formed integrally with the catheter tube or may be a separate structure which is secured to the distal end of the catheter tube, where the separate structure may be formed from the same or different material. The dilatation balloon will be located adjacent to the housing, either on the distal or the proximate side.

Referring to FIGS. 1 and 2, a vascular catheter 10 comprises a flexible catheter body 12 having a proximal end 14 and a distal end 16. A proximal housing 18 is secured to the proximal end 14 of catheter body 12 in a conventional manner, e.g., by welding or adhesives. The proximal housing will typically be formed from metal, e.g., stainless steel, or a rigid plastic and includes a first port 20 which is connected to a central lumen 22 (FIG. 2) extending the length of catheter body 12, and a second port 24 which is connected to balloon inflation lumen 26. A third port or connector 28 provides for connection of wires 30 which run to an ultrasonic transducer 32, as will be described in more detail hereinafter. Finally, the proximal housing 18 terminates with a coupling member 34 which is secured to the distal end of a flexible drive member 36. The flexible drive member 36 is typically formed of braided cable, as described in co-pending application Ser. No. 07/500,818, the disclosure of which is incorporated herein by reference, and is connected at its distal end to a rotatable mirror 38, as will be described in more detail hereinafter.

The distal end 16 of the catheter body 12 is joined by adhesives or welding to a cylindrical housing 40 including a pair of spaced-apart cylinders 42 and 44 having a gap region 46 therebetween. The housing is formed from a rigid material, e.g., stainless steel or a rigid plastic, and the individual cylinders 42 and 44 are joined by a rod 48 which spans the gap region 46, forming a relatively rigid structure. The ultrasonic transducer 32 is mounted within the forward or distal cylinder 44 and disposed to direct an ultrasonic beam in the generally rearward or proximal axial direction. The construction and use of such ultrasonic transducers are well described in the scientific and patent literature. See, e.g., U.S. Pat. No. 4,794,931, the disclosure of which has been previously incorporated herein by reference.

The housing 40 terminates with a rounded end member 50 having a fixed guide wire 52 projecting forwardly therefrom. The use and construction of fixed guide wires is also well described in the scientific and medical literature.

Rotatable mirror 38 includes an inclined reflective surface 54 on its forward face. In the embodiment of FIGS. 1 and 2, the reflective surface 45 is inclined at an angle of approximately 45° relative to the axial direction defined by the center line of the housing 40. In this way, the ultrasonic signal projected by transducer 32 is deflected at an angle of approximately 90 relative to the axial so that, as the mirror 38 is rotated, the ultrasonic signal sweeps in a generally circular scan path. Thus, a true cross-sectional image may be obtained of the area immediately surrounding the housing 40. The construction and operation of such an ultrasonic scanning system using a fixed ultrasonic transducer and a rotatable reflective element is described in U.S. Pat. No. 4,794,931, the disclosure of which has previously been incorporated herein by reference.

As an alternative to the use of a fixed ultrasonic transducer and a rotating reflective element, the catheter of the present invention could utilize other transducer systems. For example, the phased-array transducer system of U.S. Pat. No. 4,841,977, might find use with a catheter system of the present invention, although the used of phased-array transducers is generally less desirable than systems which sweep a continuous ultrasonic wave such as that illustrated and claimed herein. Alternatively, it would also be possible to directly rotate an ultrasonic transducer so that the transducer projects and receives reflected signals in the transverse direction. Such systems, however, are mechanically more complex since they require that the lead wires connected to the transducer be capable of connection at such high rotational speeds.

Referring again to FIGS. 1 and 2, a dilatation balloon 60 is located adjacent to the imaging housing 40, and may be formed from suitable thermoplastic materials, such as polyethylene, polyvinyl chloride, polyethylene terephthalate, and the like. Such materials may be irradiated to achieve a desired degree of cross-linking which limits the maximum inflation of the balloon. Additionally, the materials may be heat constricted throughout the catheter to form tight bonds with the catheter body to prevent linkage. As illustrated in FIG. 2, the material of balloon 60 may extend over the imaging housing 40 in order to cover the gap region 46 between the cylinders 42 and 44. In this way, the housing is sealed from the external environment. Of course, it is not necessary that the material of the balloon form the covering of housing 40, and the covering may be separately formed and may also be formed of a different material.

Balloon inflation lumen 26 terminates in a port 62 located in the interior of balloon 60. In this way, balloon inflation medium introduced through port 24 may be used to inflate the balloon in a conventional manner. Optionally, venting means (not illustrated) may be provided in the balloon, as described in co-pending application Ser. No. 07/290,217, the disclosure of which is incorporated herein by reference.

The interior of imaging housing 40 is isolated from the interior of balloon 60 and is connected to central lumen 22. The interior housing 40 may thus be filled through port 20 with a medium different from that used for inflating balloon 60, usually being a medium suitable for ultrasonic imaging. Suitable imaging media include water, saline, and the like.

Referring now to FIG. 3, an alternate embodiment of the distal end 16 of catheter 10 will be described. In this embodiment, a dilatation balloon 70 is located on the distal side of an imaging housing 72 which is connected to the flexible catheter body 12. Such a configuration requires that the balloon inflation lumen 26 be connected to a bypass tube 74 which can carry inflation medium across the imaging housing 72. Conveniently, bypass tube 74 can run through a hollow lumen in connecting rod 48 or on the side of tube 74.

The dilatation balloon 70 is formed about an extended flexible region 76 of the catheter which is secured to the forward end of imaging housing 72. The bypass tube 74 exits from the connecting rod 48 and passes through a short lumen formed in the extension member 76, so that the bypass tube can terminate at an open end 78 disposed within the dilatation balloon 70.

The catheter of FIG. 3 also differs in that it employs a movable guide wire 80 in place of the fixed guide wire 52 of FIGS. 1 and 2. To accommodate the movable guide wire 80, a drive cable 82 is employed having a hollow lumen therethrough. Rotating mirror 84 also includes an axial passage 86 which receives the guide wire 80 therethrough. Similarly, ultrasonic element 88 includes a central passage 90 therethrough for receiving the guide wire 80, and the extension member 76 includes a central lumen 92. In this way, the interior of dilatation balloon 70 is isolated from the interior of the imaging housing 72 so that it can be inflated with contrast medium without interfering with ultrasonic imaging. Similarly, a suitable medium for conducting ultrasonic imaging can be introduced to the housing through central lumen 22 in the catheter body 12.

The catheter of FIGS. 1 and 2 may also be modified to receive a movable guide wire. For example, the guide wire may pass through an isolated guide wire lumen in the catheter body 12 and then through a central lumen formed in rod 48. Such designs are discussed in copending application Ser. No. 07/422,935, the disclosure of which is incorporated herein by reference. Thus, movable guide wires may be utilized with designs having the dilatation balloon located either proximally or distally relative to the imaging housing.

Referring now to FIGS. 4–7, the dilatation and imaging method of the present invention employing catheter 10 will be described. Catheter 10 is positioned within a blood vessel BV so that the imaging housing 40 is disposed within a region of stenosis S. The ultrasonic imaging unit within the housing 40 can then be used to obtain cross-sectional images of the stenosed region S in a conventional manner. Information obtained from such images will allow the treating physician to properly plan a course of dilatation treatment using balloon 60 (shown in a wrapped configuration in FIGS. 4 and 5) on the catheter 10.

After sufficient imaging information is obtained, the catheter 10 is moved so that the dilatation balloon 60 is disposed within the region of stenosis S, as illustrated in FIG. 5. The dilatation balloon 60 is then inflated using a contrast medium introduced through port 20 (FIG. 1). The pressure of the inflation medium and the duration of the treatment are chosen to expand the stenosed region S to an extent determined at least in part based on the imaging information previously obtained.

After the treatment is completed, the catheter may be withdrawn, leaving the reduced stenotic region S', as illustrated in FIG. 7. Usually, however, it will be desirable to utilize the imaging portion of catheter 10 to examine the expanded stenosed region S' prior to removing the catheter 10. In this way, the condition of the blood vessel wall can be examined to determine if further treatment is required and to further determine the likelihood of abrupt reclosure of the blood vessel.

Although the foregoing invention has been described in detail for purposes of clarity of understanding, it will be obvious that certain modifications may be practiced within the scope of the appended claims.

What is claimed is:

1. A vascular catheter comprising:
   a flexible catheter body having proximal and distal ends;
   a dilatation balloon located generally at the distal end of the catheter body;
   first means for inflating the dilatation balloon with a first medium;
   an imaging housing located generally at the distal end of the catheter body and axially spaced-apart from the dilatation balloon, said imaging housing having an interior chamber;

ultrasonic scanning means disposed within the interior chamber of the housing, wherein the interior chamber is isolated from the dilatation balloon; and second means for introducing a second medium to the interior chamber, wherein said second means is isolated from the first inflating means.

2. A vascular catheter as in claim 1, wherein the ultrasonic scanning means comprises an ultrasonic transducer, and a rotatable surface capable of reflecting ultrasonic energy between the transducer and a preselected scan path circumscribing the distal end of the catheter body.

3. A vascular catheter as in claim 2, wherein the reflective surface is inclined at an angle relative to the axial direction of about 45° so that the scan path is generally circular.

4. A vascular catheter as in claim 2, wherein the reflective surface is inclined at an angle relative to the axial direction of other than 45° so that the scan path is generally conical.

5. A vascular catheter as in claim 4, wherein the scan path crosses the region circumscribing the dilatation balloon.

6. A vascular catheter as in claim 1, wherein the dilatation balloon is located on the proximal side of the ultrasonic scanning means.

7. A vascular catheter as in claim 1, wherein the dilatation balloon is located on the distal side of the ultrasonic scanning means.

8. A vascular catheter as in claim 1, further comprising a fixed guide wire attached tot he distal tip of the catheter body.

9. A vascular catheter as in claim 1, further comprising means for receiving a movable guide wire through the catheter body.

10. A vascular catheter system comprising:

a flexible catheter body having proximal and distal ends and at least two separate lumens extending therethrough;

a dilatation balloon located generally at the distal end of the catheter body, said balloon being connected to a first of the lumens;

a housing located axially adjacent to the dilatation balloon generally at the distal end of the catheter body, said housing being connected to a second of the lumens;

ultrasonic transducer located within the housing and disposed to project ultrasonic energy in a substantially axial direction;

a rotatable reflective surface located within the housing and disposed to reflect ultrasonic energy between the transducer and the region surrounding the housing;

means for rotating the reflective surface to continuously scan the ultrasonic energy in a preselected scan path about said housing; and means for introducing contrast medium into a first lumen and means for introducing an ultrasonically compatible fluid into a second lumen, whereby contrast medium can be directed to the balloon and ultrasonically compatible fluid can be directed to the housing.

11. A vascular catheter as in claim 10, wherein the reflective surface is inclined at an angle relative to the axial direction of about 45° so that the scan path is generally circular.

12. A vascular catheter as in claim 10, wherein the reflective surface is inclined at an angle relative to the axial direction of other than 45° so that the scan path is generally conical.

13. A vascular catheter as in claim 12, wherein the scan path crosses the region circumscribing the dilatation balloon.

14. A vascular catheter as in claim 10, wherein the dilatation balloon is located on the proximal side of the ultrasonic scanning means.

15. A vascular catheter as in claim 10, wherein the dilatation balloon is located on the distal side of the ultrasonic scanning means.

16. A vascular catheter as in claim 10, further comprising a fixed guide wire attached to the distal tip of the catheter body.

17. A vascular catheter as in claim 10, further comprising means for receiving a movable guide wire through the catheter body.

18. A vascular catheter system as in claim 10, further comprising an inflatable sheath around the housing, said sheath being inflated with ultrasonically-compatible fluid through the second lumen.

19. A method for treating vascular stenosis, said method comprising:

(a) positioning a catheter within a patient's vascular system so that an ultrasonic scanner in a housing located generally at the distal end of the catheter lies at a region of stenosis;

(b) filling the interior of the housing with an ultrasonically compatible fluid;

(c) obtaining an image of the stenosed region using the ultrasonic scanner while surrounded by the ultrasonically compatible fluid;

(d) repositioning the catheter so that a dilatation balloon which is axially adjacent to the ultrasonic scanner at the distal end of the catheter lies within the region of stenosis; and (e) inflating the dilatation balloon with a fluoroscopically-opaque medium to expand the stenosed region to a degree determined at least in part based on the ultrasonic image obtained in step (c).

20. A method as in claim 19, further comprising fluoroscopically imaging the dilatation balloon as it is being inflated.

* * * * *